United States Patent
Gue et al.

(10) Patent No.: US 10,197,570 B2
(45) Date of Patent: Feb. 5, 2019

(54) MICROFLUIDIC SYSTEM AND METHOD FOR ISOLATING AND QUANTIFYING AT LEAST ONE SUB-POPULATION OF CELLS FROM A POPULATION OF CELLS

(71) Applicant: CENTRE NATIONAL DE LA RECHERCHE SCIENTIFIQUE, Paris (FR)

(72) Inventors: Anne-Marie Gue, Rebigue (FR); Karine Reybier, Castanet Tolosan (FR); Jan Sudor, Toulouse (FR); Sébastien Cargou, Toulouse (FR); Armelle Montrose, Toulouse (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 406 days.

(21) Appl. No.: 14/907,540

(22) PCT Filed: Jul. 25, 2014

(86) PCT No.: PCT/IB2014/063406
§ 371 (c)(1),
(2) Date: Jan. 25, 2016

(87) PCT Pub. No.: WO2015/011674
PCT Pub. Date: Jan. 29, 2015

(65) Prior Publication Data
US 2016/0187336 A1    Jun. 30, 2016

(30) Foreign Application Priority Data

Jul. 26, 2013 (FR) ..................................... 13 57410

(51) Int. Cl.
*B01L 3/00* (2006.01)
*G01N 33/569* (2006.01)
(Continued)

(52) U.S. Cl.
CPC .. *G01N 33/56972* (2013.01); *B01L 3/502715* (2013.01); *B01L 3/502761* (2013.01);
(Continued)

(58) Field of Classification Search
None
See application file for complete search history.

(56) References Cited

U.S. PATENT DOCUMENTS 7,250,775 B1 * 7/2007 Collins ................. B01L 3/5027
324/667
8,440,093 B1 * 5/2013 Nassef ............. B01L 3/502707
216/84

(Continued)

FOREIGN PATENT DOCUMENTS

WO    2007092713 A2    8/2007

OTHER PUBLICATIONS

International Search Report dated Nov. 25, 2014, issued in corresponding International Application No. PCT/IB2014/063406, filed Jul. 25, 2014, 4 pages.

(Continued)

*Primary Examiner* — Erik B Crawford
(74) *Attorney, Agent, or Firm* — Christensen O'Connor Johnson Kindness PLLC

(57) ABSTRACT

Disclosed are a microfluidic system (1) configured to receive cell populations and further configured to simultaneously isolate and quantify at least one sub-population of cells for each cell population, and related methods of using the system. The system comprises a substrate having networks of microchannels comprising a first sorting unit configured to isolate, by magnetic attraction, cells of interest in the population in at least one first sorting microchannel. The network comprises a second unit for simultaneous sorting and counting comprising at least one second sorting micro- (Continued)

Figure 1:
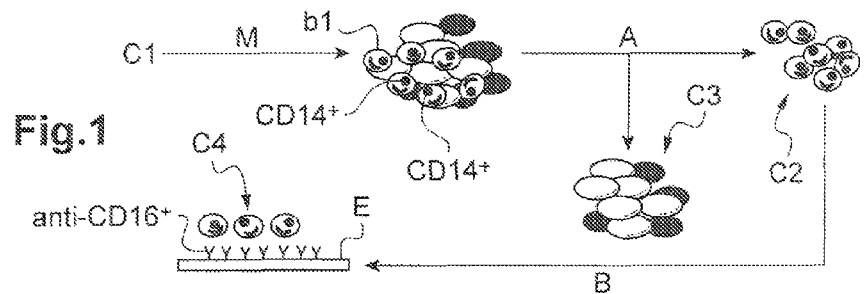

channel defined by a closed wall having an inner face provided with at least one functionalised electrode configured to trap a sub-population. The second unit further comprising means for counting the sub-population by impedance spectroscopy. The second sorting microchannel can have at least one pair of opposing functionalised electrodes and at least one pair of second micro-coils for trapping the cells of interest arranged in the wall facing the electrodes and controlling successive attraction/release cycles that alternate between the micro-coils.

18 Claims, 3 Drawing Sheets

(51) Int. Cl.
G01N 33/543 (2006.01)
G01N 15/14 (2006.01)
G01N 15/10 (2006.01)
G01N 15/12 (2006.01)
G01N 15/00 (2006.01)

(52) U.S. Cl.
CPC ..... *G01N 15/1429* (2013.01); *G01N 15/1459* (2013.01); *G01N 15/1484* (2013.01); *G01N 33/5438* (2013.01); *G01N 33/54326* (2013.01); *B01L 2200/0652* (2013.01); *B01L 2200/0668* (2013.01); *B01L 2300/0636* (2013.01); *B01L 2300/0645* (2013.01); *B01L 2300/0816* (2013.01); *B01L 2300/0861* (2013.01); *B01L 2300/0867* (2013.01); *B01L 2400/043* (2013.01); *G01N 2015/008* (2013.01); *G01N 2015/1006* (2013.01); *G01N 2015/1263* (2013.01); *G01N 2015/149* (2013.01); *G01N 2015/1486* (2013.01); *G01N 2333/70535* (2013.01); *G01N 2333/70596* (2013.01)

(56) References Cited

U.S. PATENT DOCUMENTS

2004/0132220 A1* 7/2004 Fish ................. G01N 33/54313
436/525
2005/0112544 A1* 5/2005 Xu ......................... C12M 23/12
435/4
2011/0129931 A1* 6/2011 Reboud ............. B01L 3/502753
436/63
2012/0003687 A1* 1/2012 Toner ..................... G01N 33/84
435/39

OTHER PUBLICATIONS

Written Opinion of the International Searching Authority, issued in corresponding International Application No. PCT/IB2014/063406, filed Jul. 25, 2014, 6 pages.
Chung, Y.K., et al., "An Electrical Biosensor for the Detection of Circulating Tumor Cells," Biosensors and Bioelectronics 26(5):2520-2526, Jan. 2011.
Inokuchi, H., et al., "Development of Micro Immuno-Magnetic Cell Sorting System with Lamination Mixer and Magnetic Separator," Proc. 25th Sensor Symp., Okinawa, Japan, Jan. 1, 2008, 2 pages.
Montrose, A., et al., "Développement D'un Immunocapteur Impédimétrique Pour La Détection Et La Quantification D'une Sous-Population Cellulaire: Application Au Diagnostic Précoce Des Infections," doctoral dissertation, Université Paul Sabatier, Toulouse, France, (Mar. 22, 2013), 184 pages (English Abstract).
Montrose, A., et al., "Impedimetric Immunosensor for the Detection of Circulating Pro-Inflammatory Monocytes as Infection Markers," Biosensors and Bioelectronics 49: 305-311, May 2013.
Shew, B.Y., et al., "Enhancement of Specific Cell-Capture Efficiency Using a Reversible Dielectrophoresis Field," Sensors and Actuators A: Physical 163(1):128-137, Sep. 2010.
Yang, Y., "Separating and Detecting *Escherichia coli* in a Microfluidic Channel for Urinary Tract Infection Applications," Journal of Microelectromechanical Systems 20(4): 819-827, Aug. 2011.
Fulcrand D., et al., "Development of a flexible microfluidic system integrating magnetic micro-actuators for trapping biological species," Journal of Micromechanics and Microengineering 19(10):105019, Sep. 22, 2009, 11 pages.
Mishra, N. et al. "On-chip micro-biosensor for the detection of human CD4(+) cells based on AC impedance and optical analysis," Biosensors and Bioelectronics 21(5): 696-704, Nov. 15, 2005.
Written Opinion of the International Searching Authority dated Nov. 25, 2014, issued in corresponding International Application No. PCT/IB2014/063406, filed Jul. 25, 2014, 8 pages.
International Preliminary Report on Patentability dated Jan. 26, 2016, issued in corresponding International Application No. PCT/IB2014/063406, filed Jul. 25, 2014, 1 page.

* cited by examiner

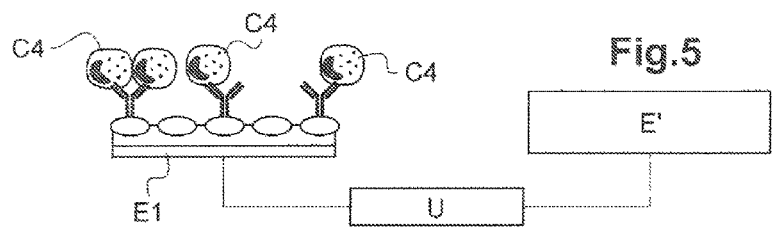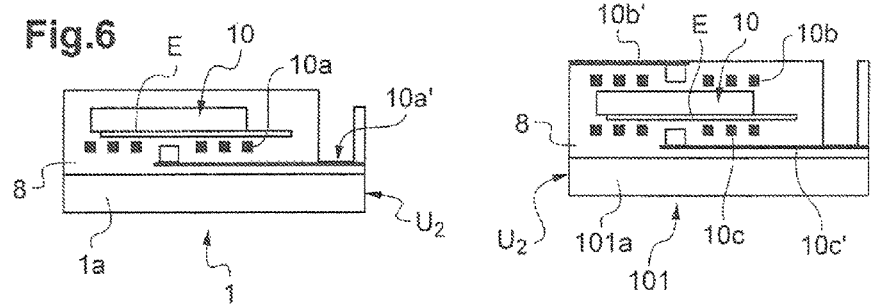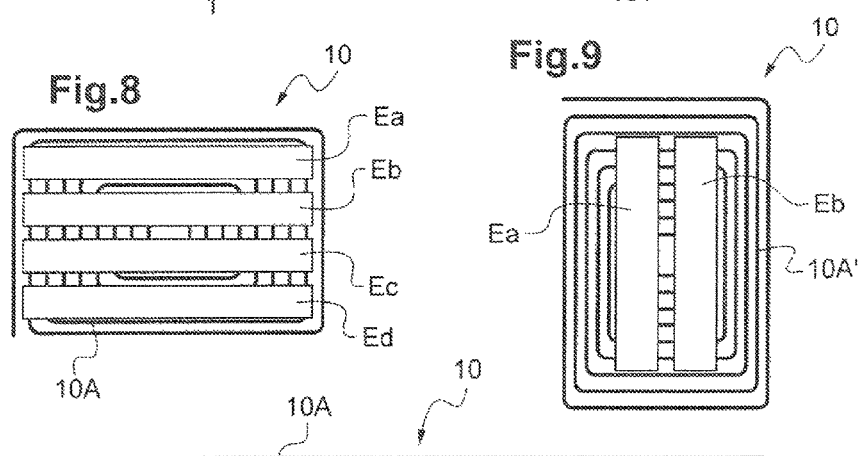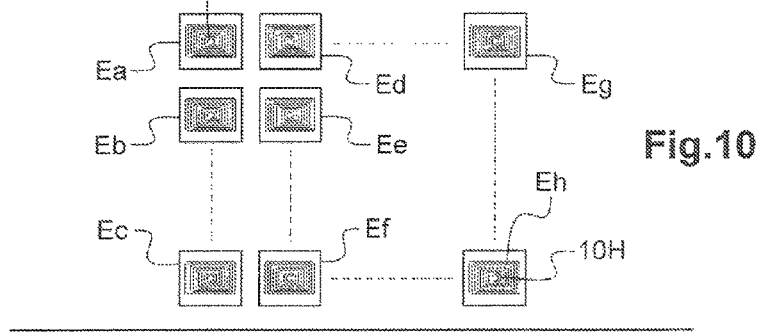

MICROFLUIDIC SYSTEM AND METHOD FOR ISOLATING AND QUANTIFYING AT LEAST ONE SUB-POPULATION OF CELLS FROM A POPULATION OF CELLS

The present invention relates to a microfluidic system capable of receiving populations of cells and capable of isolating and quantifying simultaneously for each of the populations at least one sub-population of cells, and to a method for isolating and quantifying simultaneously at least one sub-population of cells from a population of cells using this system. The invention in particular applies to the sorting of cells of interest consisting of so-called «circulating» monocytes of blood from populations of cells formed with blood samples, followed by isolation and quantification of at least one of these sub-populations formed with infected monocytes (i.e. inflammation markers). However, the invention generally applies to immunological sorting and to the counting of any circulating cells (e.g. cancer cells or marker cells for tropical and infectious diseases) or of any cells obtained by sampling a tissue and put into solution by a sole and same system integrating micro- or nano-technology techniques, for example for rapid and close medical diagnostic, the veterinary sector or even the defence sector, in a non-limiting way.

The integration to a microfluidic system of means for magnetically trapping biological compounds bound beforehand to functionalized magnetic microbeads is known, these trapping means being such that solenoid valves as microcoils obtained by electrodeposition or else as any other electrical conductor such as for example coils or wires organized as matrices. For example mention may be made for such a system of the article of R. Fulcrand, D. Jugieu, C. Escriba, A. Bancaud, D. Bourrier, A. Boukabache and A. M. Gué, Development of a flexible microfluidic system integrating magnetic micro-actuators for trapping biological species, Journal of Micromechanics and Microengineering 19 (2009) 105019.

The integration to a microfluidic system of a differential counter for selective quantification of cells, such as lymphocytes counted from a population of leucocytes present in human blood samples, is also known, by measurement of impedance and immunoaffinity chromatography. For example mention may be made of such a system of the article of Mishra N. N., Retterer S., Zieziulewicz T. J., Isaacson M., Szarowski D., Mousseau D. E., Lawrence D. A., Turner J. N., On-chip micro-biosensor for the detection of human CD4(+) cells based on AC impedance and optical analysis, Biosens Bioelectron. 2005 Nov. 15; 21(5): 696-704.

Moreover in the past, systems have been developed both for sorting and counting of cells, which use FACS («fluorescence-activated cell sorting») and flow cytometry techniques.

A major drawback of these latter sorting and counting systems lies in the constraints related to their use, which notably require heavy and bulky apparatuses, a relatively long time required for the analyses and qualified personnel. The result of this is that these systems have a high cost of use and consequently are unsuitable for regular and close follow up of patients and to a use «in the field», i.e. at the bedhead of the patient, in a medical practice, a veterinary clinic or in a tropical region, for example.

The thesis document of Armelle Montrose published on Internet: "Développement d'un immunocapteur impédimétrique poour la détection et la quantification d'une sous-population cellulaire:application au diagnostic précoce des infections" (development of an impedimetric immunosensor for detecting and quantifying a cell sub-population: application to early diagnostic of infections), Mar. 22, 2013, has a microfluidic system and a method for simultaneously isolating and quantifying a sub-population of cells using a first sorting unit for isolating by magnetic attraction of the cells of interest in a first sorting microchannel, and a second simultaneous sorting and counting unit which includes a second sorting communicating microchannel with a functionalized electrode for trapping a sub-population of cells and which includes means for counting by electrochemical impedance spectroscopy of the trapped sub-population on the functionalized electrode.

An object of the present invention is to propose a microfluidic system capable of receiving populations of cells and capable of simultaneously isolating and quantifying for each of said populations at least one sub-population of cells, said system including a substrate on which is etched a network of microchannels comprising a first sorting unit capable of isolating by magnetic attraction the cells of interest of said population of cells in at least one first sorting microchannel, this system being a remedy to the whole of the aforementioned drawbacks.

This microfluidic system is such that said network comprises a second simultaneous sorting and counting unit including at least one second sorting microchannel which directly or indirectly communicates with said at least one first sorting microchannel and which is defined by a closed wall having an internal face intended to be in contact with said cells of interest, said internal face being provided with at least one functionalized electrode capable of specifically trapping a so-called sub-population of cells from among said cells of interest, said second sorting and counting unit including means for counting by electrochemical impedance spectroscopy, said or each sub-population trapped on said at least one functionalized electrode.

For this purpose, a microfluidic system according to the invention is such that said at least one second sorting microchannel is provided with at least one pair of these functionalized electrodes laid out facing each other on two opposite sides of said internal face, and with at least one associated pair of second electrically powered trapping micro-coils which are capable of bringing the cells of interest into close contact with these functionalized electrodes, which are laid out in said wall in an adjacent way and facing said respective electrodes (i.e. laid out facing and just below the faces of the adjacent electrodes turned towards this wall) and which are capable of controlling successive and alternating attraction and release cycles between the micro-coils of said at least one pair of second micro-coils.

It will be noted that this microfluidic system according to the invention, of the laboratory-on-chip type, thus gives the possibility on a same chip of simultaneously isolating and counting easily these cell sub-populations directly by trapping them on these electrodes (this counting being achieved by impedance measurements at the trapped cell/functionalized electrode(s) interface for a wide range of frequencies), as compared with the aforementioned systems of the prior art using wieldy and costly techniques of «FACS» and of flow cytometry for sorting and counting. In particular, the miniaturization of the system according to the invention and the total integration of the counting means to this system ensures that the latter is very well adapted to sectors for which resorting to the «FACS» technique proves to be much too expensive or unsuitable, such as for example rapid and close medical diagnostic, in the veterinary sector or the defense sector.

According to another feature of the invention, said first sorting unit may comprise:
- a microchannel for bringing a so-called population of cells, which opens into said at least one first sorting microchannel,
- a microchannel for introducing magnetic means for marking said cells of interest, which opens into said at least one first sorting microchannel and into which are introduced said magnetic marking means capable of specifically binding with said cells of interest in order to form marked magnetic complexes, and
- magnetic trapping means which are laid out under said at least one first sorting microchannel and which are capable of attracting and retaining said marked magnetic complexes.

Advantageously, said magnetic marking means may comprise magnetic micro-beads or nano-beads functionalized with a first substance capable of specifically recognizing a first marker of said cells of interest, and said magnetic trapping means may comprise at least one first electrically powered micro-coil.

It will be noted that alternatively, these magnetic trapping means according to the invention may comprise any other electrical conductor such as for example coils or wires organized as matrices, in a non-limiting way.

Also advantageously, said functionalized electrodes may be functionalized with a second substance capable of specifically binding with a second marker of said sub-population to be isolated from among said cells of interest.

It will be noted that the microfluidic system of the invention thus uses differentiation based on the expression of at least two markers (e.g. antigens or receivers characteristic of the cells of interest which one wishes to isolate for example for detecting an infectious condition), by combining in this same system, the marking of the cells of interest with said magnetic marking means, the magnetic sorting of these cells of interest with said trapping means, and immunological sorting with simultaneous counting of said or each sorted sub-population from among the cells of interest in this second sorting level.

In addition to the fact that the microfluidic system of the invention may be advantageously used in a very large number of applications, as indicated above in the preamble and which allows a reduction in the volume of samples required for analysis as compared with a non-microfluidic system, it will be noted that this system is notably characterized by the sorting/counting coupling which gives it multiple advantages, among which:
- great genericity, it being specified that there may be in this system as many sorting criteria as there are immunological markers,
- very great flexibility, by means of the miniaturization of the system which, as this will be discussed hereafter, allows sorting and counting in parallel on the basis of different immunological criteria, and/or sequencing of successive sorting steps for refining a diagnostic,
- very small bulkiness, because the counting of the electric type applied by the system according to the invention does not impose association of heavy instrumentation with the second sorting unit, which may give the system substantially a format as reduced as that of a mobile telephone, making this system portable, self-sufficient in energy and optionally communicating,
- a capability of detecting very small numbers of cells in said or in each finally isolated cell sub-population (e.g. small numbers of infected cells in a very large number of normal cells), and
- reduced analysis times, since the counting of said or each cell sub-population is collective.

According to an advantageous embodiment of the invention, said internal wall face of said at least one second sorting microchannel is provided, spaced apart over its length, with a succession of several electrodes including said at least one pair of functionalized electrodes and then a non-functionalized electrode or pair of non-functionalized electrodes laid out facing each other on two opposite sides of said internal face, in order to achieve isolations and quantifications in series of several so-called cell sub-populations.

According to this embodiment of the invention, said second sorting and counting unit may comprise a plurality of said pairs of functionalized electrodes which are laid out in series (i.e. one following the other) on a same so-called second sorting microchannel or else on several of said second sorting microchannels, which are functionalized either in an identical way or not and which are associated with several individual second trapping micro-coils.

Advantageously and optionally according to this embodiment of the invention, said first sorting unit may comprise a plurality of said first sorting microchannels, and said second sorting and counting unit may comprise a plurality of said second sorting microchannels which are each provided with said at least one pair of functionalized electrodes, so that said system produces in parallel a plurality of different isolations and quantifications of said cell sub-populations from different cells of interest.

It is thus possible to mark in parallel (i.e. in different first sorting microchannels) the cells of interest with differently functionalized magnetic micro-beads or nano-beads to thereby count in parallel the different markers (i.e. in different second sorting microchannels).

Conversely, it will be noted that it is possible to successively mark and «unmark» the cells of interest for counting those having several expressed markers.

Still more advantageously in connection with this parallel creation of different isolations and quantifications, said second sorting and counting unit may comprise a plurality of said pairs of functionalized electrodes which are laid out in parallel (i.e. independently of each other) on a same so-called second sorting microchannel or else on several so-called second sorting microchannels, which are functionalized either identically or not and which are associated with as many of said pairs of individual second trapping micro-coils.

It will be noted that the microfluidic systems according to the invention may be equipped in a flexible way depending on the analyses to be made, with a variable number of said first and second micro-coils and of said functionalized and non-functionalized electrodes, which micro-coils and electrodes may have geometries and localizations which are also variable within the network of microchannels which may be branched accordingly.

According to an alternative of the invention, said second sorting and counting unit may comprise a matrix of said pairs of functionalized electrodes which are individually addressed, and which are associated with as many of said individual second trapping micro-coils.

It will be noted that this matrix of electrodes gives the possibility of optimizing the sensitivity of the counting by adapting it to the desired analysis, as compared with a single electrode or a pair of electrodes with large surface area(s).

A method according to the invention for simultaneous isolation and quantification of at least one sub-population of cells from a cell population, is characterized in that it comprises a flow of a sample comprising said cell population in a network of microchannels of a microfluidic system as defined above, with the following successive steps:

a) trapping by magnetic attraction said cells of interest in said at least one first sorting microchannel, b) removing the undesirable constituents from said sample so as to only retain said thereby trapped cells of interest, and then c) trapping said at least one sub-population of cells from among said cells of interest in said at least one second sorting microchannel by said at least one pair of functionalized electrodes, and concomitantly counting by electrochemical impedance spectroscopy said at least one trapped sub-population.

According to another feature of the invention, in step a):

it is possible to mark said cells of interest with magnetic micro-beads or nano-beads functionalized with a first substance specifically binding with a first marker of said cells of interest, in order to obtain marked magnetic complexes, and then it is possible to magnetically trap said complexes with at least one first micro-coil.

According to another feature of the invention, in step c), it is possible to attract said marked magnetic complexes with at least one pair of second trapping micro-coils, which is laid out facing said at least one pair of electrodes functionalized with a second substance specifically binding with a second marker of said at least one sub-population to be isolated, and which brings said complexes into close contact with said at least one pair of functionalized electrodes for trapping and counting this sub-population.

Advantageously, said sample containing said population of cells is a full blood sample, said cells of interest being monocytes which are magnetically isolated in step a) with said first marker expressed by the cells of interest which is an antigen for example CD14 and said first marking substance which is an antibody, for example an anti-CD14 antibody, said isolated and quantified sub-population of cells by immunological sorting in step c) comprising infected monocytes expressing said second marker which is an antigen for example CD16, said second substance being an antibody, for example an anti-CD16 antibody.

It will be noted that the detection of an infectious condition is a preferential application of the method according to the invention, and that it is carried out from blood samples via quantitative analysis of infected circulating monocytes as markers of the infection. Indeed, the so-called «circulating» monocytes of blood, which belong to the first line of defense against infections, are sub-divided in a known way into two main groups according to their expression in a CD14 receptor (receptor of lipopolysaccharide LPS) and in a CD16 receptor (Fcγ RIII receptor of low activity), it being recalled that the two main phenotypes of monocytes are CD14++ CD16− and CD14+ CD16+ and that the phenotype CD14+ CD16+ was clearly identified as being pro-inflammatory (expression of pro-inflammatory cytokines).

The counting by electrochemical impedance spectroscopy of step c) of the method according to the invention is carried out in a non-Faradic mode, i.e. in the absence of a redox probe, or else in a Faradic mode.

Figure 2:
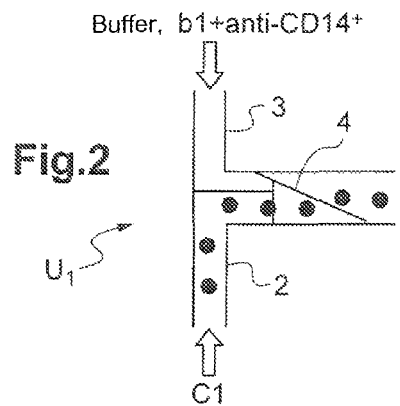
Figure 3:
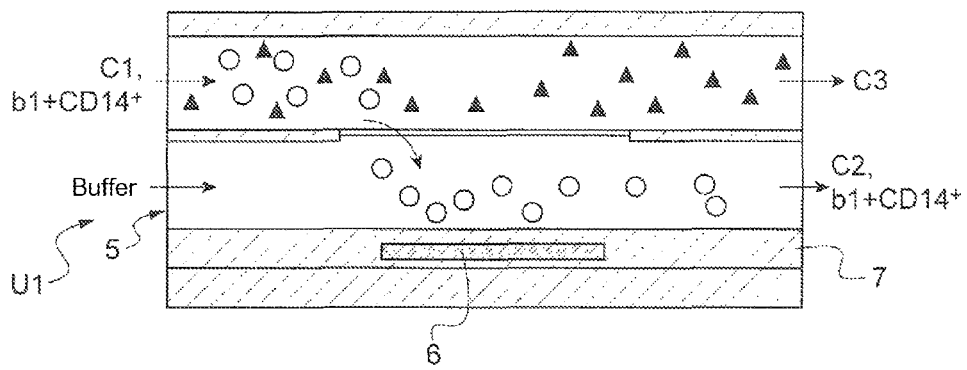
Figure 4:
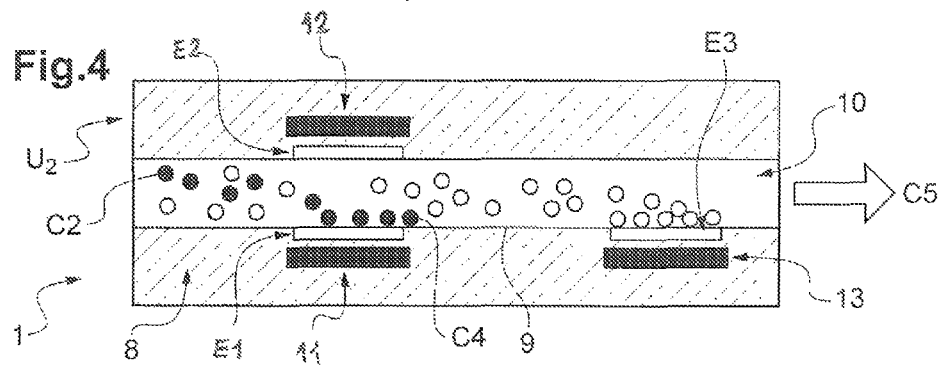
Figure 11:
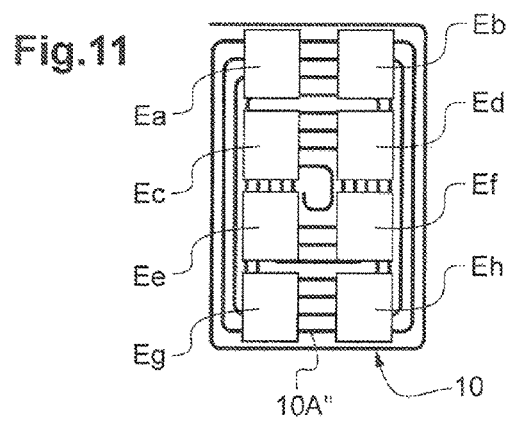
Figure 12:
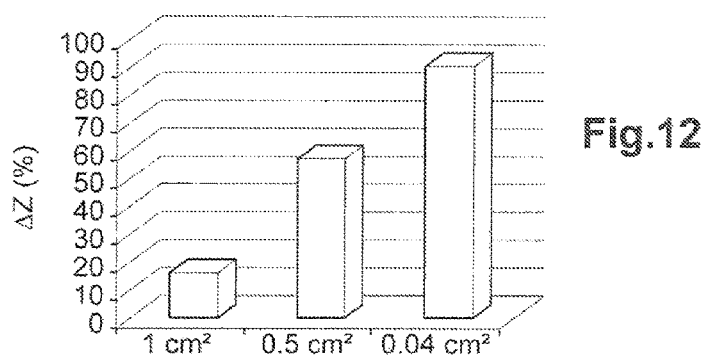
Figure 13:
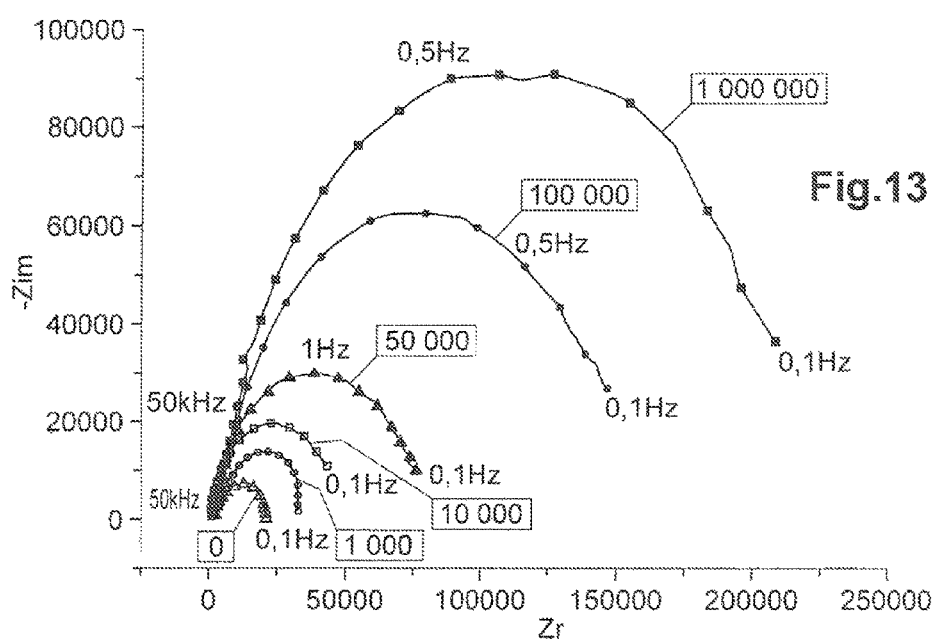

Other advantages, features and details of the invention will become apparent from the additional description which follows with reference to appended drawings, only given as examples and wherein:

FIG. 1 is a diagram illustrating the main steps of a method according to the invention for isolating and quantifying infected monocytes from a full blood sample, FIG. 2 is a schematic partly longitudinal sectional view of a microfluidic system according to the invention showing an upstream portion of the first sorting unit achieving marking of the cells of interest (e.g. monocytes) by the magnetic marking means, FIG. 3 is a schematic partly longitudinal sectional view of a microfluidic system according to the invention showing a first sorting microchannel of the first sorting unit carrying out the sorting by magnetic attraction of these cells of interest, FIG. 4 is a schematic partly longitudinal sectional view of a microfluidic system according to the invention showing a second sorting microchannel achieving isolation and counting of a sub-population of cells (e.g. infected monocytes) on a pair of functionalized electrodes and then of other cells of interest on a non-functionalized electrode, FIG. 5 is a diagram schematically illustrating the counting method by electrochemical impedance spectroscopy of the sub-population trapped in this second sorting microchannel, FIG. 6 is a schematic partly cross-sectional view of a microfluidic system according to an example of the invention showing this second sorting microchannel provided with a micro-coil associated with a functionalized electrode for trapping the sub-population, FIG. 7 is a schematic partly cross-sectional view of a microfluidic system according to another example of the invention showing, as an alternative of FIG. 6, the second sorting microchannel provided with two micro-coils associated with the functionalized trapping electrode, FIG. 8 is a schematic view showing, in a second sorting microchannel, a parallel layout of functionalized electrodes associated with a single collective trapping micro-coil, FIG. 9 is a schematic view showing as an alternative of FIG. 8, in a second sorting microchannel, a layout in series of functionalized electrodes associated with a single collective trapping micro-coil, FIG. 10 is a schematic view showing as an alternative of FIGS. 8 and 9, in a second sorting microchannel, a matrix of functionalized electrodes according to the invention which are individually addressed and which are respectively associated with trapping micro-coils, FIG. 11 is a schematic view showing as an alternative of FIG. 10, in a second sorting microchannel, a matrix of functionalized electrodes which are individually addressed and which are associated with a single collective trapping micro-coil, FIG. 12 is a bar graph illustrating the influence of the surface (area in $cm^2$ in abscissa) of a functionalized electrode according to the invention on the sensitivity of the counting measurement (expressed in ordinates by the relative impedance variation $\Delta Z$ in %), and FIG. 13 is a graph of the Nyquist diagram type illustrating the variation of imaginary impedance ($Z_{im}$, in Ohms) versus the real impedance (Zr, in Ohms) and the concentration of cells.

A microfluidic system 1, 101 according to the invention (partly visible in FIGS. 2, 3, 4, 6, 7) may be advantageously used as illustrated in FIG. 1, which relates to the preferential example of the invention applying immunological sorting of the cells of interest according to several antigens. In order to better understand the principle of the invention, the example of simultaneous sorting and counting of the infected monocytes was taken, it being specified that this example is not limiting.

A first sorting unit $U_1$ (visible in FIGS. 2 and 3) is, by a first sorting operation A, intended to remove at best the constituents of a full blood sample C1 in order to only retain the monocytes C2 forming the cells of interest in this example. This sorting operation A is carried out subsequently to a step for marking M by means of magnetic micro- or nano-beads b1 functionalized with antibodies capable of recognizing the C2 monocytes (such as for example, anti-CD14 antibodies may recognize the corresponding antigen CD14 expressed by all the monocytes C2). The bead/blood cells mixture is produced on the device 1, 101 via microchannels as slots, for example. The thereby marked monocytes C2 are then retained during a first sorting operation T with at least one first electrically powered micro-coil 6 and laid out under a first sorting microchannel 5 (see FIG. 3), while the other constituents C3 of the full blood C1 (such as granulocytes, lymphocytes, red corpuscles, notably) are eluted.

The marked monocytes C2 are then released and brought towards a second sorting and counting unit $U_2$ (visible in FIGS. 4 and 6-7), where they are sorted more specifically (second sorting step B) depending on other antigens expressed at their surface (such as for example the antigen CD16 expressed by the infected monocytes C4 forming the sub-population to be isolated and to be quantified) and counted. According to the contemplated application, several antigens may be targeted in parallel.

In this second unit $U_2$, the infected monocytes C4 are trapped inside a second sorting microchannel 10 on a functionalized electrode E (see FIGS. 1, 5, 6 and 7) or else on a pair of functionalized electrodes E1 and E2 facing each other in the example of FIG. 4, the functionalization being achieved with an antibody capable of binding with an antigen of interest (for example an anti-CD16 antibody for the CD16 antigen of the infected monocytes C2). In order to maximize trapping, a single second micro-coil 10a is installed below the electrode E or else, according to the invention, a pair of second electrically powered micro-coils 11 and 12 respectively around functionalized electrodes facing each other E1 and E2, in order to attract the infected monocytes C4 on the electrodes E or E1, E2 and thus increase their probability of interaction with their functionalized surface. The cells not specifically attached onto these electrodes E or E1, E2 are then released and optionally attracted on other electrodes functionalized by other antibodies, depending on the desired application.

The infected monocytes C4 or more generally said or each sub-population C4 of cells trapped on the corresponding functionalized electrode are counted by means of the electrically insulating property of this sub-population C4, by electrochemical impedance spectroscopy.

FIGS. 6 and 7 show as a cross-section two microfluidic systems 1, 101 according to the invention which comprise a substrate 1a, 101a and which integrate:
  for the one of FIG. 6, said or each functionalized electrode E (for example in gold) coating the internal face 9 of said or each microchannel 10 and associated with a single micro-coil 10a for example in copper which is integrated to the wall 8 of the microchannel 10 below this internal face 9, and
  for the one of FIG. 7, said or each electrode E (for example in gold) which is associated with two micro-coils 10b and 10c for example also in copper, these micro-coils 10b and 10c being integrated to the wall 8 of said or each microchannel 10 on either side of the latter (i.e. above and below the upper and lower sides of its internal face 9 of rectangular section).

The wall 8 of said or each microchannel 10 is for example made in a photosensitive polymer (e.g. of the SU8 type).

Further, in FIGS. 6 and 7, the electric connections 10a', 10b', 10c' (e.g. in copper) are visible respectively for powering the micro-coils 10a, 10b, 10c.

More specifically in connection with the first sorting unit $U_1$, in FIG. 2 it is seen that the step M for marking the cells of interest C2 (e.g. monocytes) is applied by mixing by means of two separate microchannels 2 and 3 which respectively convey in the lower microchannel 2, the population of cells C1 to be analysed (e.g. full blood) and, in the upper microchannel 3, a buffer solution containing the magnetic micro- or nano-beads b1 functionalized beforehand a t the surface with antibodies for example anti-CD14 antibodies. It is possible to use optionally active or passive mixtures, as well as optionally an encapsulation of the beads b1 and of the cells in drops, for example. These microchannels 2 and 3 join up in a junction area 4 opening into the first sorting microchannel 5 visible in FIG. 3 within the first sorting unit $U_1$.

The application of the sorting operation A by magnetic attraction is thus visible in FIG. 3, which is carried out by means of the micro-coil 6 which is laid out outside the microchannel 5, for example by being integrated to the closed wall 7 of this microchannel 5. The activation of the micro-coil 6 gives the possibility of trapping beads b1/monocyte C2 complexes.

Said or each first sorting microchannel 5 is then rinsed in order to remove all the constituents of the blood C3 other than the thereby trapped monocytes C2. This purification step simply allows removal of all the non-desired species, in order to obtain a solution for which the physico-chemical properties are known and under control. After this rinsing, the beads b1/monocyte C2 complexes are released into the solution and are carried away by the flow towards the second sorting and counting unit $U_2$.

In the example of FIG. 4, it is seen that this unit $U_2$ comprises the pair of functionalized electrodes E1 and E2 on the internal face 9 of the closed wall 8 of a second sorting microchannel 10, and the associated pair of micro-coils 11 and 12 in order to attract, from the whole of the marked complexes, the infected monocytes C4 onto these electrodes E1 and E2. These micro-coils 11 and 12 are for example integrated to the wall 8 (thus being positioned outside the space internal to the microchannel 10) and attract these infected monocytes C4 expressing the CD16 antigens into close contact with the surface of these functionalized electrodes, in this example by the anti-CD16 antibodies. During deactivation of the micro-coils 11 and 12, only the monocytes expressing the CD16 antigens and having established antigen-antibody interactions remain attached on the electrodes E1 and E2, the other monocytes C5 being carried away by the downstream flow of the microchannel 10. After this trapping of the infected monocytes, their number is directly counted by the aforementioned technique of impedance spectroscopy.

Generally, it will be noted that the probability of trapping said or each sub-population to be quantified, such as these infected monocytes, may be maximized in different ways. In particular, the layout of both micro-coils 11 and 12 respectively below and above the microchannel 10 gives the possibility of achieving successive and alternating attraction-release cycles between both micro-coils 11 and 12 for obtaining maximum trapping efficiency. Alternatively or as a combination with this preferential layout of electrodes E1 and E2 facing each other, it is possible to provide several functionalized electrodes and associated coils which are positioned one after the other, in order to «catch up» with the cells which would not have been trapped by these functionalized electrodes.

Finally and so as to determine the CD16+/CD14+ ratio of the monocytes, said or each second sorting microchannel 10 according to the invention may further be provided, always on the internal face 9 of its wall 8, with at least one ultimate non-functionalized electrode E3 coupled with at least one ultimate micro-coil 13 facing it positioned in this wall 8, out of the space internal to the microchannel 10. In this way, it is possible to immobilize by magnetic trapping on this electrode E3 the CD14+ monocytes which are not immunologically trapped by the electrodes E1 and E2 provided upstream, and to count these CD14+ monocytes with the same impedance spectroscopy technique.

FIG. 5 illustrates this counting technique by electrochemical impedance spectroscopy (EIS), which consists of measuring the impedance of the interface between said or each functionalized electrode E1, E2 and the layer of cells trapped at its surface (e.g. layer of infected monocytes C4), by imposing a small alternating potential U difference and by measuring the current resulting from this at various frequencies, by means of a counter-electrode or reference electrode E'. The impedance Z is given by the voltage U/current I ratio and is given in a known way by the formula $Z=U/I=|Z| (\cos \phi + i \sin \phi)$.

Electrochemical impedance spectroscopy is of particular interest in the case of cell layers, the cells having excellent electrically insulating properties. A change in impedance may either result from a change in the coverage level of the electrode E, E1, E2 (this is the case when a cell adheres, grows, dies or migrates at the surface of the electrode), or a variation of the electrically insulating property of the cell layer C4. Therefore, by measuring the impedance Z at the cell C4/electrode E, E1, E2 interface for a wide range of frequencies, it is possible, by modelling of the obtained diagrams (Nyquist diagrams $Zim=f (Zr)$) in an equivalent electric circuit consisting of resistors and capacitors, to infer the coverage level of the cells and therefore the number of trapped cells C4.

Two distinct methods exist for these measurements:

The impedance measurements conducted in the presence of a redox species which plays the role of a probe ($Fe(CN)_6^{3-/4-}$ for example). In this case, the capability of the probe of being reduced or oxidized at the electrode E, E1, E2 is inferred from impedance measurements by evaluating the resistance to charge transfer which varies depending on the more or less electrically insulating nature of the deposited cell layer. In this case, this is referred to as Faradic impedance; and The measurements conducted in a «neutral» medium (e.g. in a buffer solution or a culture medium) which give the possibility of accessing the phenomena occurring at the cell film. In this case this is referred to as non-Faradic impedance, and it is in this case, the resistance of the film which changes over time in the presence of the trapped cells.

In the present invention, it is the impedance measurement in a non-Faradic mode which is preferentially applied for counting the cells C4 trapped on the electrode E1, E2, because this measurement proves to be more sensitive.

FIGS. 8-11 illustrate examples of a layout of functionalized electrodes Ea, Eb, Ec, Ed, Ee, Ef, Eg, Eh, etc. in a microfluidic system 1,101 according to the invention. These electrodes Ea, . . . , Eh may be provided in separate microchannels 10 but also in a same microchannel 10.

In FIG. 8, the electrodes Ea, Eb, Ec, Ed, either identically functionalized or not, are laid out in parallel while being associated with a collective trapping micro-coil 10A (according to the invention, individual trapping micro-coils may be used).

In FIG. 9, the electrodes Ea, Eb, either functionalized identically or not, are laid out in series while being associated with a collective trapping micro-coil 10A' (according to the invention individual trapping micro-coils may be used).

In FIG. 10, the electrodes Ea, . . . , Eh, either identically functionalized or not, are laid out as a matrix, individually addressed and associated with individual trapping micro-coils 10A, . . . , 10H.

In FIG. 11, the electrodes Ea, . . . , Eh, either identically functionalized or not, are laid out as a matrix, individually addressed and associated with a collective trapping micro-coil 10A".

According to the size of each electrode Ea, . . . , Eh, an "analogue" operation (obtained signal proportional to the number of trapped cells) or "digital" operation may be contemplated. Indeed, as the electrode has a size of the order of magnitude of that of the cell, it then only detects one cell at a time and the signal will therefore be binary: 1 or 0.

The Applicant conducted tests dealing with the sensitivity of the counting by electrochemical impedance spectroscopy at each electrode E, E1, E2, according to the area of the latter (FIG. 12), as well as with the variation of impedance measured according to the number of trapped cells on each of these electrodes E, E1, E2.

The graph of FIG. 12 shows that the sensitivity of the measurement for the counting of each sub-population of cells C4 according to the invention (variation of impedance measured in % for this counting) is all the higher since the area of each functionalized trapping electrode E, E1, E2 is more reduced (area of 0.04 cm$^2$ for the maximum value of $\Delta Z$ close to 90%).

The graph of FIG. 13 (with the frequencies used varying between 0.1 Hz and 50 kHz for the lowest impedances on the bottom left) shows that the measured impedance is all the higher since the concentration of cells on the electrode E, E1, E2 is greater, as shown by the values of concentrations of cells (framed) which appear on the side of each curve and which attain 1,000,000 for the upper curve (as compared with the lower curve relating to zero concentration of cells, and of the intermediate curves where the number of cells is successively 1,000, 10,000, 50,000 and 100,000).

The Applicant further varied, for two diameters of the microbeads b1 used for the marking (2.3 Ξm and 4.5 µm), the flow pressure (from 5 to 10 mbars) and the number of active micro-coils in the second sorting microchannel 10 (from one to three micro-coils, with a 100 mA intensity of the power supply current of the micro-coils), for comparing according to these parameters the efficiency of the deviation and of the trapping or the separation of the sole magnetic microbeads according to the pressure of the flow stream in the microfluidic system 1,101.

The obtained results are listed in the tables hereafter.

TABLE 1

| beads with a diameter of 2.3 µm | |
|---|---|
| Pressure | Separation |
| 5 mbars | 87% |
| 6 mbars | 86.5% |
| 7 mbars | 73% |

At 10 mbars, one has very high flow velocity and zero trapping.

TABLE 2 beads with a diameter of 4.5 μm, pressure of 7 mbars

| Number of active micro-coils | Trapping | Separation |
|---|---|---|
| 1 | 80% | 100% |
| 2 | 100% | 100% |
| 3 | 100% | 100% |

TABLE 3 beads with a diameter of 4.5 μm, pressure of 8 mbars

| Number of active micro-coils | Trapping | Separation |
|---|---|---|
| 1 | 0% | 74% |
| 2 | 32% | 71% |
| 3 | 42% | 88% |

These results notably show the advantage of using at least two active micro-coils and a flow pressure comprised between about 5 mbars and 8 mbars, in order to apply the isolation and counting method according to the invention.

The invention claimed is:

1. A microfluidic system configured to receive populations of cells and configured to simultaneously isolate and quantify for each of said populations at least one sub-population of cells expressing a first marker having affinity for a second substance, said system including a substrate in which is etched a network of microchannels comprising a first sorting unit comprising magnetic trapping means to isolate by magnetic attraction magnetic microbeads bound to cells of interest of said population of cells in at least one first sorting microchannel, said network comprising a second simultaneous sorting and counting unit including at least one second sorting microchannel which directly or indirectly communicates with said at least one first sorting microchannel and which is defined by a closed wall having an internal face intended to be in contact with said cells of interest bound to said magnetic microbeads, said internal face being provided with at least one pair of electrodes functionalized with said second substance to specifically trap said sub-population of cells from among said cells of interest bound to said magnetic microbeads, said second sorting and counting unit including counting means by electrochemical impedance spectroscopy of said or each sub-population trapped on said pair of electrodes, wherein said at least one pair of said electrodes laid out facing each other on two opposite sides of said internal face, and with at least one associated pair of second electrically powered trapping micro-coils which are configured to bring said cells of interest bound to said magnetic microbeads in close contact with said electrodes, which are laid out in said wall and facing said respective electrodes to command successive and alternating attraction and release cycles between the micro-coils of said at least one pair of second micro-coils.

2. The microfluidic system according to claim 1, wherein said first sorting unit comprises:

a first microchannel for bringing the populations of cells which opens into said at least one first sorting microchannel, and a second microchannel configured to receive said magnetic microbeads and introduce said magnetic microbeads into said at least one first sorting microchannel which specifically bind with said cells of interest.

3. The microfluidic system according to claim 2, said system comprising said magnetic micro-beads functionalized with a first substance capable of specifically recognizing a first marker of said cells of interest, and wherein said magnetic trapping means comprise at least one first electrically powered micro-coil.

4. The microfluidic system according to claim 3, wherein the first marker is CD14, and wherein the first substance is an anti-CD14 antibody.

5. The microfluidic system according to claim 1, wherein the second marker is CD16, and wherein the second substance is an anti-CD16 antibody.

6. The microfluidic system according to claim 1, wherein said internal face of the wall of said at least one second sorting microchannel is provided spaced out on its length with a succession of several electrodes including said at least one pair of functionalized electrodes and then an additional non-functionalized electrode or pair of additional non-functionalized electrodes laid out facing each other on two opposite sides of said internal face in order to achieve isolations and quantifications in series of several sub-populations of cells.

7. The microfluidic system according to claim 6, wherein said second sorting and counting unit comprises a plurality of said pairs of functionalized electrodes which are laid out in series on a same said second sorting microchannel or on several second sorting microchannels, which are either functionalized identically or not and which are associated with several said pairs of second individual trapping micro-coils.

8. The microfluidic system according to claim 1, wherein said first sorting unit comprises a plurality of said first sorting microchannels, and wherein said second sorting and counting unit comprises a plurality of said second sorting microchannels which are each provided with said at least one pair of functionalized electrodes so that said system produces in parallel a plurality of different isolations and quantifications from said sub-populations of cells from different cells of interest.

9. The microfluidic system according to claim 8, wherein said second sorting and counting unit comprises a plurality of said pairs of functionalized electrodes which are laid out in parallel on a same said second sorting microchannel or on several second sorting microchannels, which are either functionalized identically or not and which are associated with as many of said pairs of second individual trapping micro-coils.

10. The microfluidic system according to claim 1, wherein said second sorting and counting unit comprises a matrix of said pairs of functionalized electrodes which are individually addressed and which are associated with as many said second individual trapping micro-coils.

11. A method for simultaneous isolation and quantification of at least one sub-population of cells from a cell population, wherein the method comprises the step of generating a flow of a sample comprising said cell population in the network of microchannels of the microfluidic system according to claim 1, with the following successive steps:

(a) trapping by magnetic attraction said cells of interest in said at least one first sorting microchannel;

(b) removing undesirable constituents of said sample in order to only retain the thereby trapped cells of interest; and (c) trapping said at least one sub-population of cells from among said cells of interest in said at least one second sorting microchannel by said at least one pair of functionalized electrodes and concomitant counting by electrochemical impedance spectroscopy of said at least one trapped sub-population.

12. The isolation and quantification method according to claim 11, wherein in step (a):
said cells of interest are marked with the magnetic microbeads functionalized with a first substance specifically binding with a first marker of said cells of interest, for obtaining marked magnetic complexes; and
said complexes are magnetically trapped by the magnetic trapping means comprising at least one first micro-coil.

13. The isolation and quantification method according to claim 12, wherein in step (c), said marked magnetic complexes are attracted by said at least one pair of second trapping micro-coils which is laid out facing said at least one pair of electrodes functionalized with a second substance specifically binding with a second marker of said at least one sub-population of cells to be isolated, and which brings said complexes into close contact with said at least one pair of functionalized electrodes for trapping and counting the at least one trapped sub-population of cells.

14. The isolation and quantification method according to claim 13, wherein said sample containing said population of cells is a full blood sample, said cells of interest being monocytes which are magnetically isolated in step (a) with said first marker expressed by the cells of interest which is an antigen and said first marking substance which is an antibody, said sub-population of cells isolated and quantified by immunological sorting in step (c) comprising infected monocytes expressing said second marker which is an antigen, said second substance being an antibody.

15. The isolation and quantification method according to claim 11, wherein the counting by electrochemical impedance spectroscopy of step (c) is carried out in a non-Faradic mode.

16. The isolation and quantification method according to claim 11, wherein the counting by electrochemical impedance spectroscopy of step (c) is carried out in a Faradic mode.

17. The isolation and quantification method according to claim 14, wherein the antigen of the first marker is CD14, and wherein the antibody of the first substance is an anti-CD14 antibody.

18. The isolation and quantification method according to claim 14, wherein the antigen of the second marker is CD16, and wherein the antibody of the second substance is an anti-CD16 antibody.

* * * * *